United States Patent
Johnson et al.

(10) Patent No.: US 9,856,450 B2
(45) Date of Patent: Jan. 2, 2018

(54) CLOSED SYSTEM FOR EXTRACTING ISOLATED MEDIUM

(71) Applicant: SAINT-GOBAIN PERFORMANCE PLASTICS CORPORATION, Solon, OH (US)

(72) Inventors: Scott R. Johnson, Troy, NY (US); Michael S. Block, Hudson, OH (US); Christopher J. Pates, Eagle, CO (US); Avery A. Hallett, Castleton-on-Hudson, NY (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 20 days.

(21) Appl. No.: 14/963,156

(22) Filed: Dec. 8, 2015

(65) Prior Publication Data

US 2016/0160173 A1    Jun. 9, 2016

Related U.S. Application Data

(60) Provisional application No. 62/089,042, filed on Dec. 8, 2014.

(51) Int. Cl.
*C12M 1/00*    (2006.01)

(52) U.S. Cl.
CPC .................................. *C12M 47/04* (2013.01)

(58) Field of Classification Search
CPC ....... C12M 47/04; C12M 35/00; C12M 37/04
See application file for complete search history.

(56) References Cited

U.S. PATENT DOCUMENTS

| 6,345,640 B1 | 2/2002 | Newberg |
| 7,124,914 B2 | 10/2006 | Foster et al. |
| 7,389,792 B2 | 6/2008 | Newberg |
| D615,166 S | 5/2010 | Patti |
| 8,445,264 B2 | 5/2013 | Seubert et al. |
| 2012/0248111 A1 | 10/2012 | Bear et al. |

FOREIGN PATENT DOCUMENTS

| DE | 202014001074 U1 | 5/2014 |
| EP | 0365756 A1 | 5/1990 |
| EP | 2503007 A1 | 9/2012 |
| EP | 2743332 A1 | 6/2014 |
| JP | 2012044876 A | 3/2012 |
| WO | 2012122603 A1 | 9/2012 |

OTHER PUBLICATIONS

International Search Report issued in Application No. PCT/US2015/064566 dated Mar. 23, 2016, 1 page.

*Primary Examiner* — Shogo Sasaki
(74) *Attorney, Agent, or Firm* — Chi S. Kim; Abel Law Group, LLP

(57) ABSTRACT

An assembly includes an adjustable dip tube that can selectively withdraw an isolated component at various heights within a vessel. The adjustable nature of the dip tube can improve the cell recovery rate as compared to conventional cell recovery assemblies. Additionally, the assembly can take advantage of the adjustable nature of the dip tube while maintaining an aseptic interior cavity of the assembly.

10 Claims, 9 Drawing Sheets

CLOSED SYSTEM FOR EXTRACTING ISOLATED MEDIUM

CROSS-REFERENCE TO RELATED APPLICATION(S)

This application claims priority under 35 U.S.C. §119(e) to U.S. Patent Application No. 62/089,042 entitled "ADJUSTABLE DIP TUBE," by Scott R. Johnson, et al., filed Dec. 8, 2014, which is assigned to the current assignee hereof and incorporated herein by reference in its entirety.

FIELD OF THE DISCLOSURE

The present disclosure relates to volume reduction assemblies.

RELATED ART

Centrifugation can be used to separate or isolate different components of a sample based on characteristics such as mass, density, and the like. In many applications, an isolated component of the sample needs to be recovered for further analysis or purification. There exists a need for a process and an apparatus that enables high yield removal of an isolated component of a sample. Additionally, there exists a need for a process and apparatus that enables removal of an isolated component of a sample without compromising the surrounding environment.

BRIEF DESCRIPTION OF THE DRAWINGS

Embodiments are illustrated by way of example and are not limited in the accompanying figures.

Figure 1:
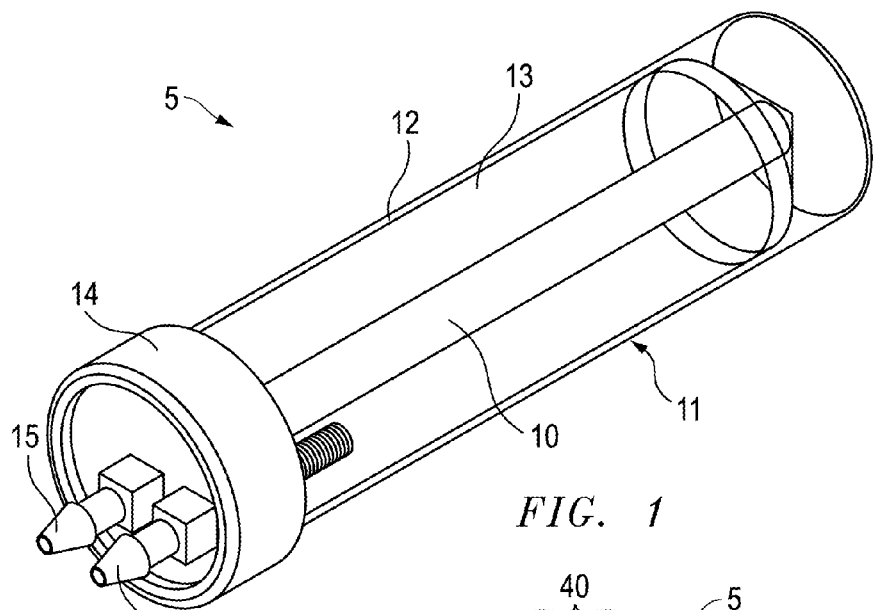
FIG. 1 includes an illustration of an embodiment of an assembly described herein.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the dip tube and cell recovery arts.

Embodiments described herein can include a closed system for extracting isolated medium. The closed system can include a vessel, a cap on the vessel, and tube adapted to withdraw an isolated component within the vessel. The term "selectively withdraw" refers to preferentially withdrawing one component over another. In certain embodiments, the tube can be an adjustable tube adapted to withdraw an isolated component at various heights within the vessel. The adjustable nature of the tube can improve the cell recovery rate as compared to conventional cell recovery assemblies. In other embodiments, the tube can be fixed at a height selected so as to improve the cell recovery rate as compared to conventional cell recovery assemblies.

Additionally, embodiments of the assembly and method described herein can withdraw an isolated component within a vessel while maintaining an aseptic interior cavity of the vessel. In certain embodiments, the assembly is adapted to reduce the volume of a composition comprising a media and a biologically active substance, and recover the biologically active substance. In particular embodiments, the assembly and method can selectively withdraw the biologically active substance at various heights to improve its cell recovery rate while maintaining an aseptic environment. Embodiments of the assembly will be described in more detail below.

Figure 2:
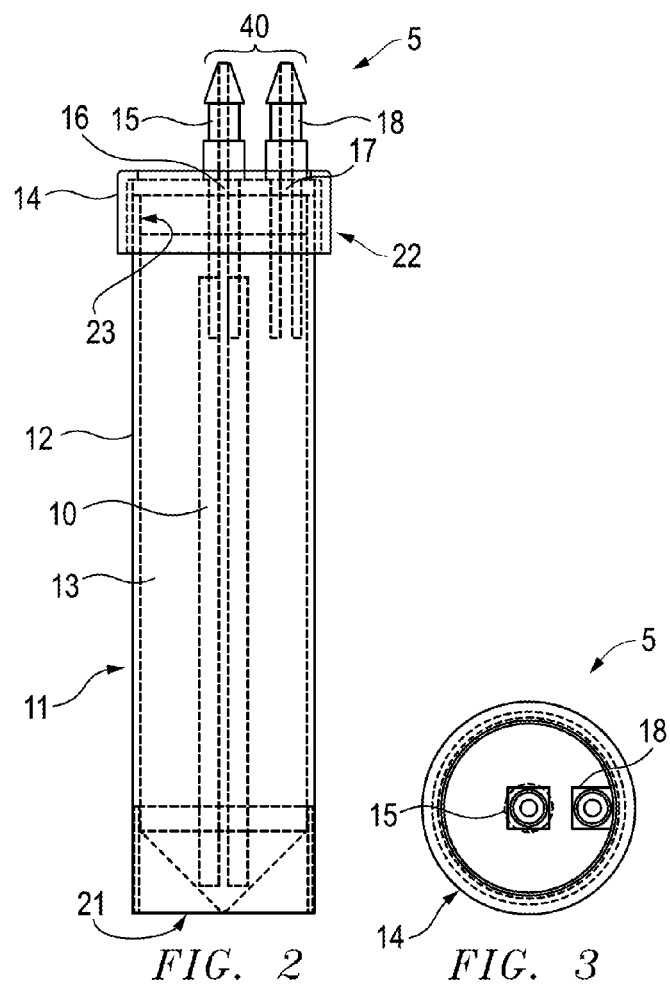
FIG. 2 includes a side-view illustration of an embodiment of FIG. 1.
Figure 3:
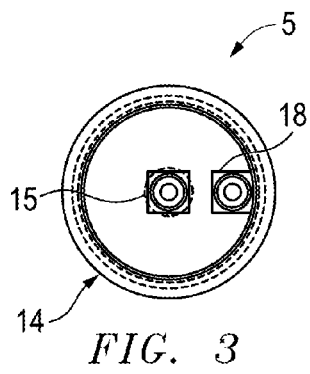
FIG. 3 includes a top-view illustration of an embodiment of FIG. 1.

FIGS. 1-3 include illustrations of embodiments of an assembly 5. As illustrated in FIG. 1, the assembly 5 can include a tube 10 disposed in a vessel 11. The vessel 11 can include a sidewall 12 defining a cavity 13. The tube 10 can be disposed adjacent the sidewall 12 defining the cavity 13, such as within the cavity 13 defined by the sidewall 12. Further, the assembly 5 can include a cap 14 and a port 15. As illustrated in FIG. 2, the cap 14 can define a bore 16, such as a bore extending through the thickness of the cap 14 and the port 15 can engage the cap 14 adjacent the bore 16. In certain embodiments, the tube 10 can engage the port 15 via the bore 16 in the cap. The assembly 5 can also include a bore 17, such as a bore extending through the thickness of the cap 14, and can include a port 18 disposed adjacent the bore 17.

The vessel 11 can include a variety of types of vessels adapted to contain a fluid. The vessel can be adapted to withstand centrifugation. The sidewall 12 of the vessel 11 can include a sidewall of a polyhedron shape or a non-polyhedron shape. As illustrated in FIG. 2, the sidewall 13 can include a cylindrical sidewall. In particular embodiments, the vessel 11 can include a conical tube, a beaker, a flask, or the like. In more particular embodiments, the vessel 11 can have a volume of at least 50 mL. In particular embodiments, the vessel 11 can have a volume of up to 50 mL, up to 250 mL, or up to 500 mL, or even up to 1000 mL. For example, the vessel 11 can include a conical tube having a volume of up to 50 mL, up to 250 mL, up to 500 mL, or even up to 1000 mL.

The vessel 11 can comprise a closed end 21 and an open end 22. In certain embodiments, the closed end 21 can be opposite, such as directly opposite, the open end 22. The closed end 21 can be a flat end, a rounded end, a pointed end, and the like. The open end 22 can include an opening having a maximum width $W_V$ across the opening in a range of 0.3 inches to 3 inches, such as 0.4 inches to 2.5 inches, or even 0.5 inches to 2 inches. The maximum width of the opening can be calculated by measuring the maximum distance from one side of the opening to another side of the opening or, when appropriate, by measuring the maximum diameter of the opening. The vessel 11 can have a maximum height $H_V$ measured from the closed end 21 of the vessel 11 to the open end 22 of the vessel 11. In certain embodiments, the value for $H_V$ of the vessel can be at least 3 inches, such as at least 3.5 inches, or even at least 4 inches. In further embodiments, the value for $H_V$ may be no greater than 10 inches, such as no greater than 8 inches, or even no greater than 6 inches. For example, the value for $H_V$ can be in a range of any of the above minimum and maximum values, such as 3 to 10 inches, 3.5 to 8 inches, or 4 to 6 inches.

The open end 22 of the vessel 11 can include an attachment surface 23, such as a clasping surface, a threaded surface, and the like. The attachment surface 23 can be disposed on an interior surface of the vessel 11, an exterior surface of the vessel 11, or both.

Figure 4:
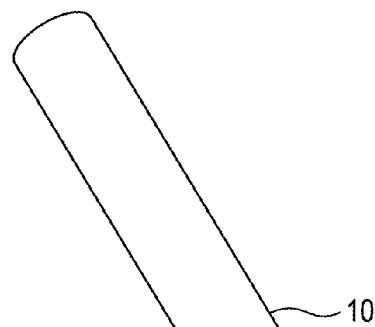
FIG. 4 includes an illustration of an embodiment of a tube described herein.
Figure 5:
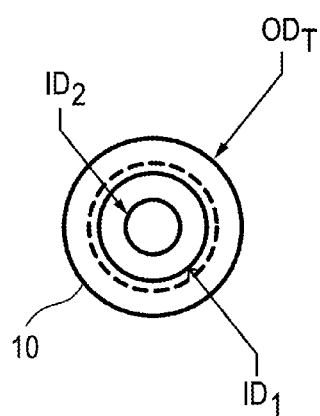
FIG. 5 includes a top-view illustration of an embodiment of a tube described herein.
Figure 6:
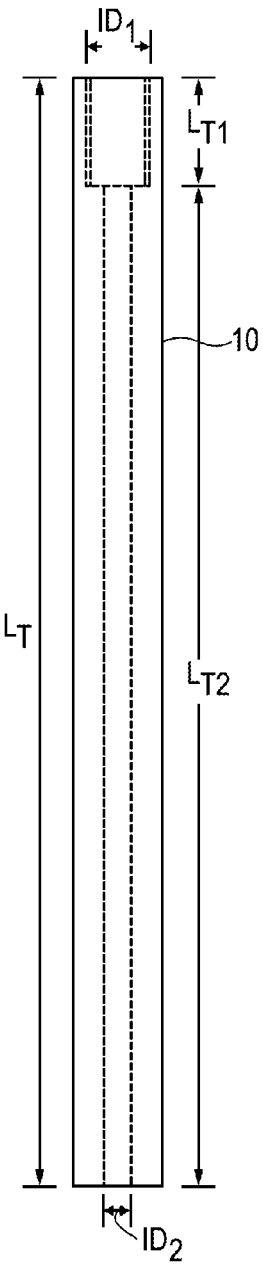
FIG. 6 includes a side-view illustration of an embodiment of a tube described herein.

The vessel 11 can comprise a variety of materials, such as a metal, a ceramic, a plastic, and the like, In certain embodiments, the vessel can comprise a plastic, such as a polyester, a polyethylene terephthalate, a polyethylene, a polyvinyl chloride, a polypropylene, a polystyrene, a polyamide, a polyacrylate, a polycarbonate, a polyurethane, or any combination thereof. FIGS. 4-6 include illustrations of certain embodiments of the tube 10. The tube 10 can be a dip tube. The tube can be adapted to handle biologically active material. The tube 10 can comprise a rigid material, such as a plastic. In certain embodiments, the tube 10 can include a plastic material. The plastic material can include a polyester, a polyethylene terephthalate, a polyethylene, a polyvinyl chloride, a polypropylene, a polystyrene, a polyamide, a polyacrylate, a polycarbonate, a polyurethane, or any combination thereof. In particular embodiments, the plastic material can be free of animal-derived components. In more particular embodiments, the plastic material can be free of diethylhexyl phthalate (DEHP) or even free of any phthalate. Moreover, the plastic material can be sterilizable, such as sterilizable via gamma rays.

Figure 18:
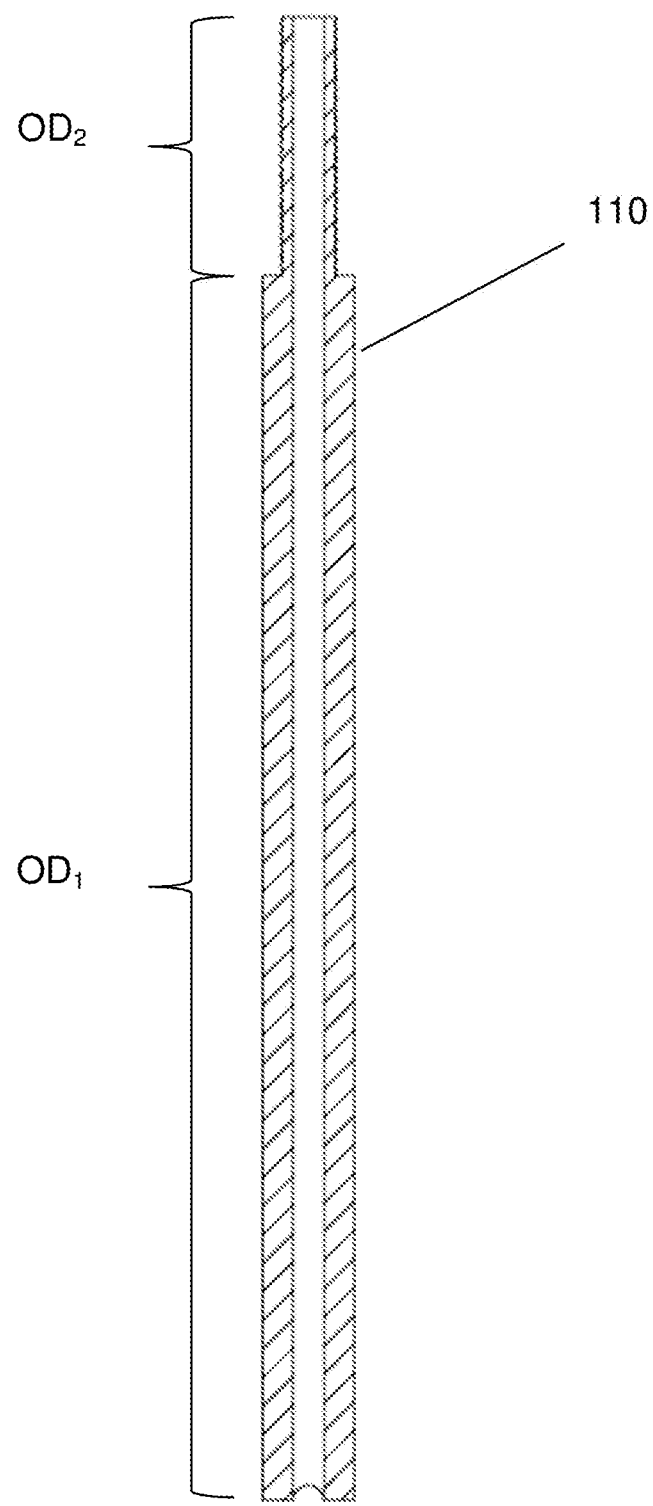
FIG. 18 includes a cross-sectional view illustration of a tube according to an embodiment disclosed herein.

As stated previously, the closed system can include a dynamic mechanism that can adjust the tube 10 to selectively withdraw an isolated component from the cavity 13 at various heights. In certain embodiments, the adjustable nature of the tube 10 can be related to a dynamic mechanism disposed on an inner diameter of the tube 10 (or the outer diameter of the tube 110, as illustrated in FIG. 18). The dynamic mechanism can include a threaded surface.

As illustrated in FIG. 4, the tube 10 can have an outer diameter $OD_T$ sufficient for the desired application. In certain embodiments, the value for $OD_T$ can be at least 0.01 inches, such as at least 0.05 inches, or even at least 0.07 inches. In further embodiments, the value for $OD_T$ may be no greater than 3 inches, such as no greater than 1 inch, or even no greater than 0.5 inches. For example, the value for $OD_T$ can be in a range of any of the above minimum and maximum values, such as 0.01 to 3 inches, 0.05 to 1 inches, or 0.07 to 0.5 inches.

The tube 10 can have an inner diameter $ID_T$ sufficient for the desired application. In certain embodiments, the value for $ID_T$ can be at least 0.01 inches, such as at least 0.04 inches, or even at least 0.08 inches. In further embodiments the value for $ID_T$ may be no greater than 0.8 inches, such as no greater than 0.5 inches, or even no greater than 0.3 inches. For example, the value for $ID_T$ can be in a range of any of the above minimum and maximum values, such as 0.01 to 0.8 inches, 0.04 to 0.5 inches, or 0.08 to 0.3 inches.

As illustrated in FIGS. 5 and 6, in certain embodiments, the tube 10 can include a multimodal inner diameter. The multimodal inner diameter of the tube can include a bimodal inner diameter including a larger inner diameter $ID_1$ and a smaller inner diameter $ID_2$. In particular embodiments, the multimodal inner diameter can be employed to accommodate an adjustment mechanism adapted to adjust the height of the tube when in use. For example, the inner diameter $ID_1$ can include a threaded surface adapted to engage with the threaded surface of the tube port 15.

In certain embodiments, the value of $ID_1$ can be at least 1.1 times greater than the value of $ID_2$, such as at least 1.3 times greater than the value of $ID_2$, or even at least 1.5 times greater than the value of $ID_2$. In further embodiments, the value of $ID_1$ may be no more than 4 times greater than the value of $ID_2$, such as no more than 3 times greater than the value of $ID_2$, or even no more than 2.5 times greater than the value of $ID_2$. For example the value for $ID_1$ can greater than $ID_2$ by a multiple in a range of any of the above minimum and maximum values, such as 1.1 to 4, 1.3 to 3, or 1.5 to 2.5.

In further embodiments, the value of $ID_1$ can be at least 0.08 inches, such as at least 0.12 inches, or even at least 0.15 inches. In yet further embodiments, the value of $ID_1$ may be no greater than 0.5 inches, such as no greater than 0.3 inches, or even no greater than 0.25 inches. For example the value for $ID_1$ can be in a range of any of the above minimum and maximum values, such as 0.08 to 0.5 inches, 0.12 to 0.3 inches, or even 0.15 to 0.25 inches.

In still further embodiments, the value of $ID_2$ can be at least 0.01 inches, such as at least 0.02 inches, or even at least 0.03 inches. In yet still further embodiments, the value of $ID_2$ may be no greater than 0.3 inches, such as no greater than 0.2 inches, or even no greater than 0.1 inches. For example the value for $ID_2$ can be in a range of any of the above minimum and maximum values, such as 0.01 to 0.3 inches, 0.02 to 0.2 inches, or even 0.03 to 0.2 inches.

In certain embodiments, as illustrated in FIGS. 13 to 15 and 18, the tube 110 can include a multimodal outer diameter. The multimodal outer diameter of the tube can include a bimodal outer diameter including a larger outer diameter $OD_1$ and a smaller outer diameter $OD_2$. In particular embodiments, the multimodal outer diameter can be employed to accommodate an adjustment mechanism adapted to adjust the height of the tube when in use. For example, the smaller outer diameter $OD_2$ can include a threaded surface adapted to engage with the threaded surface of the tube port 115.

In certain embodiments, the value of $OD_1$ can be at least 1.1 times greater than the value of $OD_2$, such as at least 1.3 times greater than the value of $OD_2$, or even at least 1.5 times greater than the value of $OD_2$. In further embodiments, the value of $OD_1$ may be no more than 4 times greater than the value of $OD_2$, such as no more than 3 times greater than the value of $OD_2$, or even no more than 2.5 times greater than the value of $OD_2$. For example the value for $OD_1$ can greater than $OD_2$ by a multiple in a range of any of the above minimum and maximum values, such as 1.1 to 4, 1.3 to 3, or 1.5 to 2.5.

In further embodiments, the value of $OD_1$ can be at least 0.08 inches, such as at least 0.9 inches, or even at least 0.1 inches. In yet further embodiments, the value of $OD_1$ may be no greater than 0.5 inches, such as no greater than 0.3 inches, or even no greater than 0.25 inches. For example the value for $OD_1$ can be in a range of any of the above minimum and maximum values, such as 0.08 to 0.5 inches, 0.9 to 0.3 inches, or even 0.1 to 0.25 inches.

In still further embodiments, the value of $OD_2$ can be at least 0.05 inches, such as at least 0.06 inches, or even at least 0.07 inches. In further embodiments, the value of $OD_2$ may be no greater than 0.3 inches, such as no greater than 0.2 inches, or even no greater than 0.1 inches. For example the value for $OD_2$ can be in a range of any of the above minimum and maximum values, such as 0.05 to 0.3 inches, 0.06 to 0.2 inches, or even 0.07 to 0.2 inches.

Referring to FIG. 6, the tube 10 can have a length $L_T$ measured from a first end of the tube 10 to an opposite second end of the tube 10. In certain embodiments, the value for $L_T$ can be at least 1 inch, such as at least 2 inches, or even at least 3 inches. In further embodiments, the value for $L_T$ may be no greater 10 inches, such as no greater than 7 inches, or even no greater than 5 inches. For example the value for $L_T$ can be in a range of any of the above minimum and maximum values, such as 1 to 10 inches, 2 to 7 inches, or 3 to 5 inches.

The tube 10 can have a first portion comprising a first end and second portion comprising an opposite second end. In certain embodiments, the first portion of the tube 10 can comprise the first mode having $ID_1$ and the second portion of the tube 10 can comprise the second mode having $ID_2$. In particular embodiments, the first end of the tube 10 can have $ID_1$ and include the dynamic mechanism. In further particular embodiments, the second end of the tube 10 can have $ID_2$ and be adapted to first contact the biologically active material when used to handle biologically active material.

In other embodiments, the tube 10 can be a fixed dip tube set at a height selected to withdraw the isolated component from the cavity 13 at a specific height.

Figure 7:
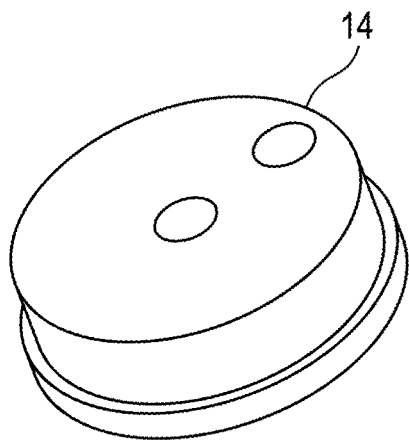
FIG. 7 includes an illustration of an embodiment of a cap described herein.
Figure 8:
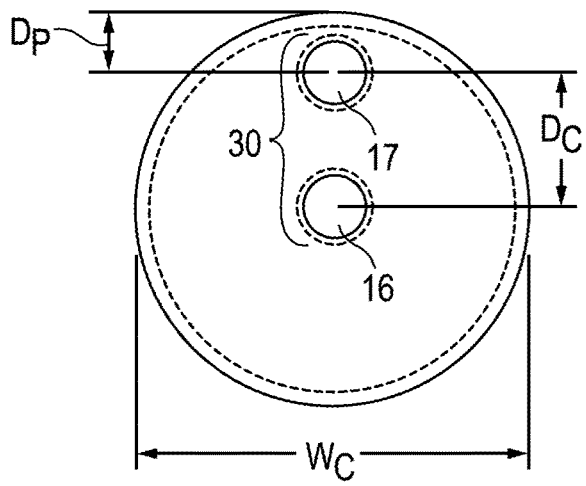
FIG. 8 includes a top-view illustration of an embodiment of a cap described herein.
Figure 9:
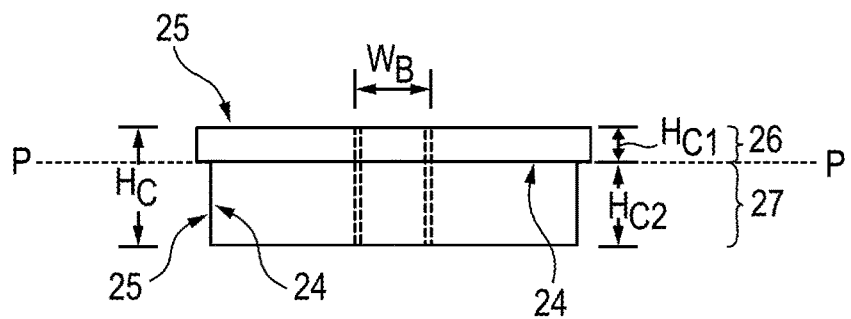
FIG. 9 includes a side-view illustration of an embodiment of a cap described herein.

FIGS. 7-9 include illustrations of embodiments of the cap 14. The cap 14 can be disposed adjacent the open end of the vessel 11 and adapted to maintain an aseptic environment within the cavity 13, even while the tube 10 selectively withdraws an isolated component from the cavity 13 at various heights.

The cap 14 can be removably attached to vessel 11 or permanently attached to the vessel 11. The cap 14 can comprise any one or more of the materials discussed above with respect to the vessel 11. The cap 14 can include the same material as the vessel 11 or a different material than the vessel 11.

Referring to FIG. 8, the cap 14 can have a maximum width $W_C$ measured along the plane P. The maximum width $W_C$ can be equal to a diameter of the cap 14. In certain embodiments, the value for $W_C$ can be at least 0.5 inches, such as at least 0.7 inches, or even at least 0.9 inches. In further embodiments, the value for $W_C$ may be no greater than 7 inches, such as no greater than 5 inches, or no greater than 3 inches. For example, the value for $W_C$ can be in a range of any of the above minimum and maximum values, such as 0.5 to 7 inches, 0.7 to 5 inches, or 0.9 to 3 inches.

In further embodiments, the value for $W_C$ can be the maximum width (or diameter) of the top portion 26, the maximum width (or diameter) of the bottom portion 27, or the maximum widths of both the top portion 26 and the bottom portion 27. In certain embodiments, the maximum width of the top portion 26 is substantially equal to or equal to the maximum width of the bottom portion 27. In further embodiments, the value for $W_C$ is equal to the maximum width of the top portion 26 and the maximum width of the bottom portion 27 is less than the maximum width of the top portion 26. In particular embodiments, the difference between the maximum width of the top portion 26 and the maximum width of the bottom portion 27 can be at least 0.03 inches, such as at least 0.05 inches, or even at least 0.07 inches. In further embodiments, the difference may be no greater than 0.2 inches, such as no greater than 0.1 inches, or even no greater than 0.09 inches. For example, the difference can be in a range of any of the above minimum and maximum values, such as 0.03 to 0.2 inches, 0.05 to 0.1 inches, or 0.07 to 0.09 inches.

Referring to FIG. 9, the cap 14 can have an interior surface 24 and an opposite exterior surface 25, relative to the cavity 13 of the vessel 11. In other words, when the cap 14 is attached to the vessel 11, the interior surface 24 faces toward the cavity 13 and the opposite exterior surface 25 faces away from the cavity 13.

In certain embodiments, the cap 14 can have a variety of shapes depending on the desired application. In particular embodiments, the cap 14 can have a circular shape. The cap can have a top portion 26 and a bottom portion 27, relative to the closed end 21 of the vessel 11, such that the bottom portion 27 of the cap 14 is closer to the closed end 21 of the tube 10 than the top portion 26 of the cap 14. In certain embodiments, the top portion 26 and the bottom portion 27 can lie along a plane P where the top portion 26 can extend from the plane P away from the closed end 21 of the tube 10 and the bottom portion 27 can extend from the plane P toward the closed end 21 of the tube 10. In particular embodiments, the open end 21 of the tube 10 also lies along the plane P and the top portion 26 of the cap 14 extends above the open end 21 of the tube 10 (away from the closed end 21 of the tube 10) and the bottom portion 27 of the cap 14 extends below the open end 22 of the tube 10 (toward the closed end 21 of the tube 10).

The cap 14 can have a height $H_C$ measured from the bottom edge of the bottom portion 27 of the cap 14 to the top edge of the top portion 26 of the cap 14. In certain embodiments, the value for $H_C$ can be at least 0.1 inches, such as at least 0.2 inches, or even at least 0.3 inches. In further embodiments, the value for $H_C$ can be at least 1 inch, such as at least 0.7 inches, or even at least 0.5 inches. For example, the value for $H_C$ can be in a range of any of the above minimum and maximum values, such as 0.1 to 1 inches, from 0.2 to 0.7 inches, or 0.3 to 0.5 inches.

In further embodiments, the value for $H_C$ can be the sum of the height of the top portion 26, $H_{C1}$, and the height of the bottom portion 27, $H_{C2}$. The value for $H_{C1}$ can be the same as the value for $H_{C2}$, greater than the value for $H_{C2}$, or less than the value for $H_{C1}$. In particular embodiments, the value for $H_{C2}$ is greater than the value for $H_{C1}$ by a ratio of at least 1.5:1, such as at least 2:1, or even at least 3:1. In further embodiments, the ratio may be no greater than 7 to 1, such as no greater than 6:1, or even no greater than 5:1. For example, the ratio can be in a range of any of the above minimum and maximum values, such as 1.5:1 to 7:1, 2:1 to 6:1, or 3:1 to 5:1.

In certain embodiments, an interior surface 25 of the cap 14 can include an attachment surface. The attachment surface can include one or more of a variety of attachment surfaces adapted to attach the cap 14 to the vessel 11. In particular embodiments, the attachment surface attaches the cap 14 to the vessel 11 in a manner sufficient to maintain an aseptic environment within vessel 11, such as to maintain an aseptic environment within the cavity 13 of the vessel 11. In particular embodiments, the attachment surface can include a threaded surface and the open end 22 of the vessel 11 can include a corresponding threaded surface.

The top portion 26 of the cap 14 can have a thickness $T_C$ measured from the exterior surface 24 facing away from the cavity 13 of the vessel 11 to the interior surface 25 facing toward the cavity 13 of the vessel 11. In certain embodiments, the top portion 26 of the cap 14 can define a bore structure 30 that includes one bore or a plurality of bores. In certain embodiments, a bore of the bore structure 30 can extend into the thickness $T_C$, such as through the entire thickness $T_C$. The one or more bores of the bore structure 30 can be adapted to permit a fluid connection between the cavity 13 and an exterior environment outside the tube 10.

In certain embodiments, the bore structure 30 can include a bore having a maximum width $W_B$. In particular embodiments, the value for $W_B$ can be at least 0.05 inches, such as at least 0.1 inches, or even 0.15 inches. In further particular embodiments, the value for $W_B$ may be no greater than 1 inch, such as no greater than 0.5 inches, or even no greater than 0.3 inches. For example, the value for $W_B$ can be in a range of any of the above minimum and maximum values, such as 0.05 to 1 inch, 0.1 to 0.5 inches, or 0.15 to 0.3 inches.

The location of the bore or bores of the bore structure 30 on the top portion 26 of the cap 14 can be determined by the desired application. In certain embodiments, the bore structure 30 can include a center bore 16 located in the center of the cap, such as concentric with the cap. In particular embodiments, the center bore 16 can include a tube bore sized so as to engage the tube 10, either directly or indirectly via a port.

Referring again to FIG. 8, the bore structure 30 can include an off-center bore 17 located a distance $D_C$ from the center of the cap to the center of the off-center bore 17, or a distance $D_P$ from the perimeter of the cap to the center of the off-center bore 17. In particular embodiments, the value for $D_C$ can be at least 0.1 inches, such as at least 0.2 inches, or even at least 0.3 inches. In further particular embodiments, the value for $D_C$ may be no greater than 1 inch, no greater than 0.7 inches, or no greater than 0.5 inches. For example, the value for $D_C$ can be in a range of any of the above minimum and maximum values, such as 0.1 inches to 1 inch, 0.2 to 0.7 inches, or 0.3 to 0.5 inches. Furthermore, in certain embodiments, the value for $D_P$ can be at least 0.05 inches, such as at least 0.1 inches, or even at least 0.15 inches. In further particular embodiments, the value for $D_P$ may be no greater than 0.5 inches, no greater than 0.4 inches, or no greater than 0.3 inches. For example, the value for $D_C$ can be in a range of any of the above minimum and maximum values, such as 0.05 inches to 0.5 inches, 0.1 to 0.4 inches, or 0.15 to 0.3 inches. In particular embodiments, the off-center bore 17 can include a vent bore sized so as to engage a filter, either directly or indirectly via a port.

When the bore structure includes both a center bore 16 and an off-center bore 17, the off-center bore 17 can have a maximum width $W_{B2}$ equal to, substantially equal to, greater than, or less than the maximum width $W_{B1}$ of the center bore 16. In particular embodiments, the value for $W_{B1}$ may be different than the value for $W_{B2}$ by no greater than 30%, such as no greater than 25%, or even no greater than 20%. In further particular embodiments, the value for $W_{B1}$ may be different than the value for $W_{B2}$ by at least 5%, such as at least 10%, or even at least 15%. In yet further particular embodiments, the value for $W_{B1}$ can be different than the value for $W_{B2}$ by a percentage in a range of any of the above minimum and maximum percentages, such as 5-30%, 10-25%, or 15-20%.

Figure 10:
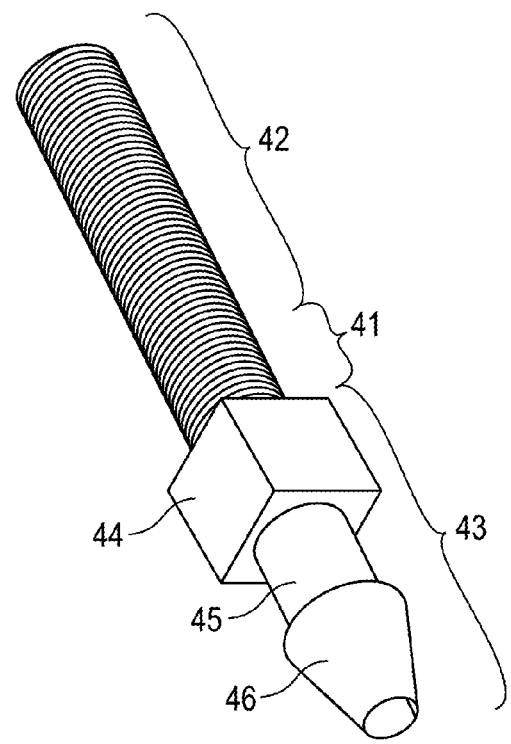
FIG. 10 includes an illustration of an embodiment of a port described herein.
Figure 11:
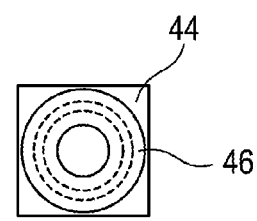
FIG. 11 includes a top-view illustration of an embodiment of a port described herein.
Figure 12:
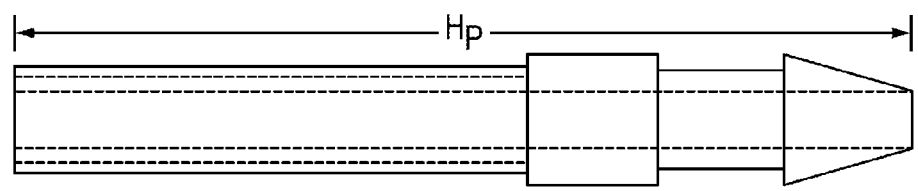
FIG. 12 includes a side-view illustration of an embodiment of a port described herein.
Figure 13:
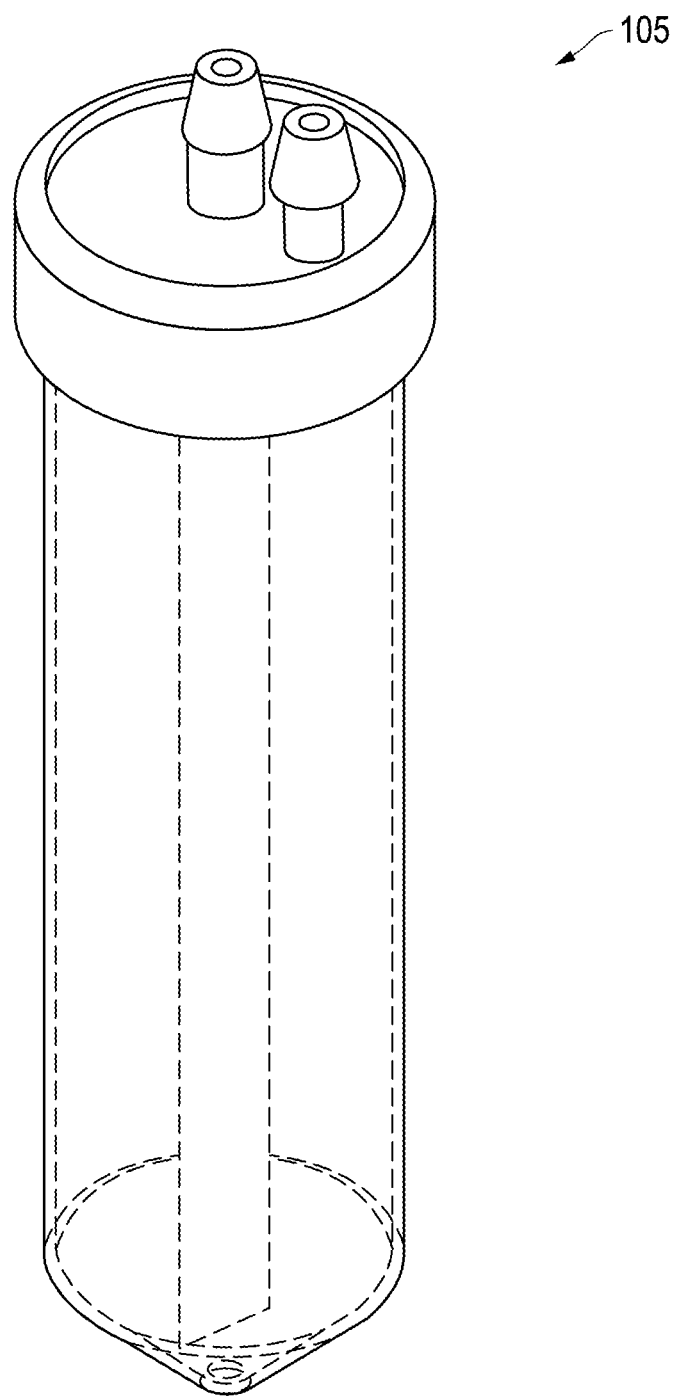
FIG. 13 includes an illustration of another embodiment of an assembly described herein.
Figure 14:
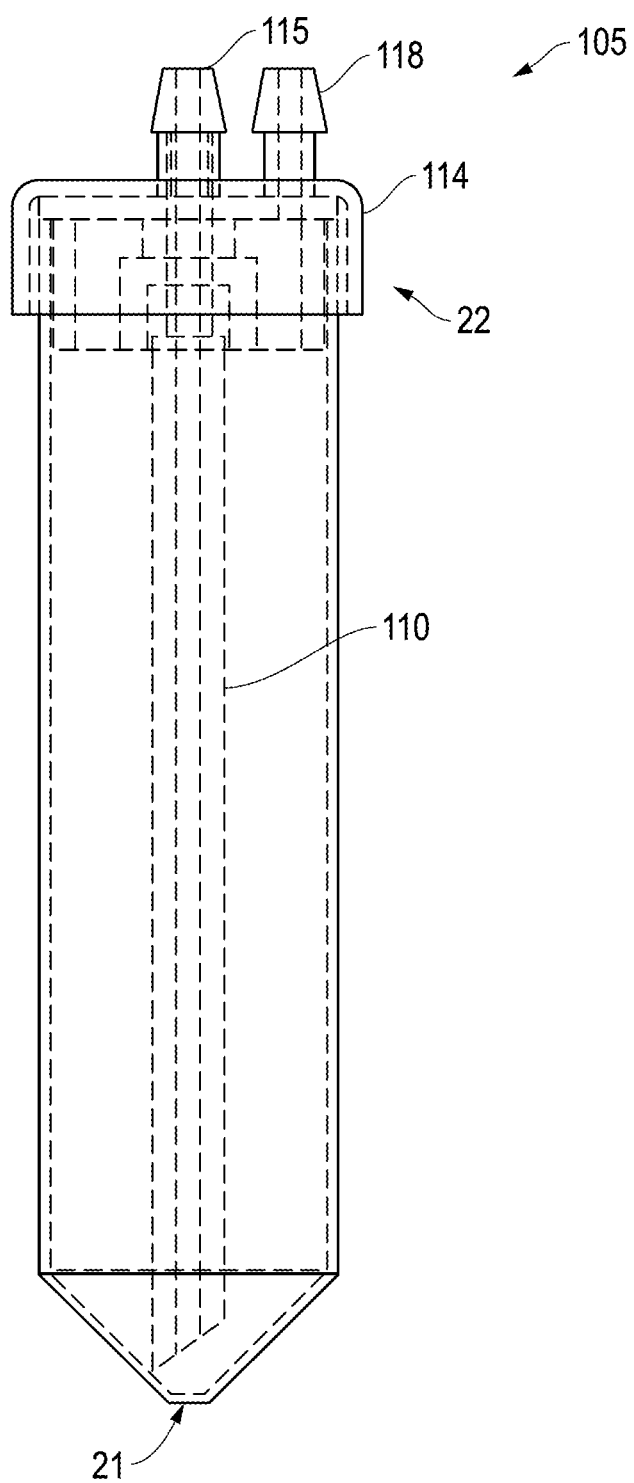
FIG. 14 includes a side-view illustration of the embodiment of FIG. 13.
Figure 15:
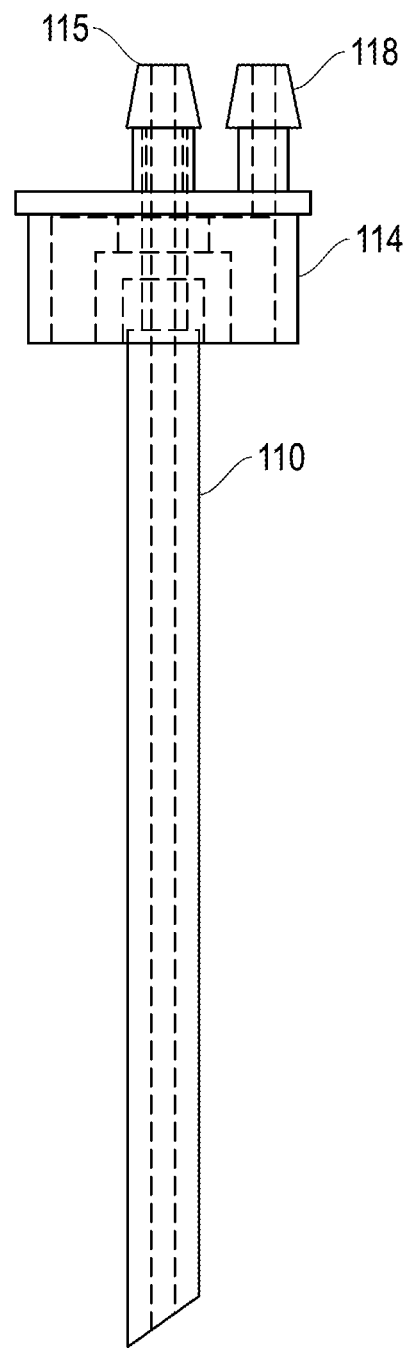
FIG. 15 includes a side-view illustration of the cap and tube of the embodiment of FIG. 13.

FIGS. 10-12 include illustrations of embodiments of a port. As stated previously, one or more bores of the bore structure 30 can be indirectly engaged with other members, such as a tube, a vent, a filter, and the like. As illustrated in FIG. 2, a port structure 40 can be included in the assembly to assist in such indirect engagement. The port structure 40 can facilitate a connection, such as a fluid connection, between the cavity 13 of the vessel 11, or a structure within the cavity 13 of the vessel 11, with an exterior environment outside the vessel 11, or a structure in an exterior environment outside the vessel 11. In particular embodiments, the port structure 40 can maintain the fluid connection between the cavity 13 and an exterior environment while at the same time maintaining an aseptic environment within the cavity 13 of the vessel 11. The port structure 40 can include any number of ports, such as a number corresponding to the number of bores defined by the top portion 26 of the cap 14.

The port structure 40 can include one or more ports, each disposed within a corresponding bore of the bore structure 30. The port can be sized so as to maintain an aseptic environment within the cavity 13 of the vessel 11. In certain embodiments, one or more ports of the port structure 40 can engage with a tube, a vent, or a filter. For example, the assembly 5 can include a tube port 15 and a vent port 18. The tube port 15 can be engaged with the tube bore 16 and maintain a fluid connection with the tube 10.

In certain embodiments, the tube port 15 can include a dynamic mechanism that enables extending the tube 10 toward the closed end 21 of the vessel 11 (i.e., further into the cavity 13), or retracting the tube 10 away from the closed end 21 of the vessel 11. The dynamic mechanism of the tube port 15 can correspond to or complement the dynamic mechanism of the tube 10. For example, the dynamic mechanism of the tube 10 can engage with the dynamic mechanism of the tube port 15 to enable the adjustable nature of the tube 10. In particular further embodiments, the dynamic mechanism of the tube port 15 can include a threaded surface that corresponds to a threaded surface of the tube 10, and the threading of the tube port 15 can engage with the threading of the tube 10 to adjust the height of the tube 10 relative to the closed end 21 of the vessel 11. In particular embodiments, the tube port 15 can be activated, such as rotated, to adjust the height of the tube 10 relative to the closed end 21 of the vessel 11 to selectively withdraw an isolated component from the cavity 13 at various heights and improve the recovery of the isolated medium as discussed below. In particular embodiments, the dynamic mechanism of the tube port 15 can be adapted to maintain the aseptic environment of the cavity 13 of the vessel 11, even when the tube 10 is being extended or retracted as described above.

In certain embodiments, as illustrated in FIG. 2, the threaded portion of the tube port 15 can extend into the interior cavity. In other embodiments, as illustrated in FIGS. 14 to 17, the cap 114 can include a cavity for receiving the tube 110. When the tube 110 is fully distended, the bottom of the port 115 comes into contact with the cap 114 so that it hits a dead-stop and can no long move downward. When raising the tube 110, the top of the non-threaded $OD_1$ of the tube 110 can hit a dead-stop on the cavity of the tube cap 114. These two dead-stops can maintain the tube within a set range of movement.

Further, the aseptic environment can be maintained as the cap 114 separates out the threaded section of tube 110 which moves within an internal threaded area of the cap 114 and the threaded section of tube 110 which moves out of the cap 114. This way, the external threaded section of tube that engages with the port 115 outside the cap 114 never enters into the same area as the internal threaded section of tube 110 that extends into the internal cavity of the vessel 11.

In other embodiments, the tube port can include a static mechanism that enables fixing the tube at a specific height relative to the closed end of the vessel. For example, the static mechanism of the tube can engage with the static mechanism of the tube port to fix the tube at the specific height. In more particular embodiments, the static mechanism of the tube port can engage with the tube to fix the height of the tube relative to the closed end of the vessel. In particular embodiments, the specific height of the tube relative to the closed end of the vessel can be configured to selectively withdraw an isolated component from the cavity and improve the recovery of the isolated component as discussed below. In more particular embodiments, the static mechanism of the tube port can be adapted to maintain the aseptic environment of the cavity of the vessel, even when the tube is withdrawing the isolated component as described herein.

Figure 16:
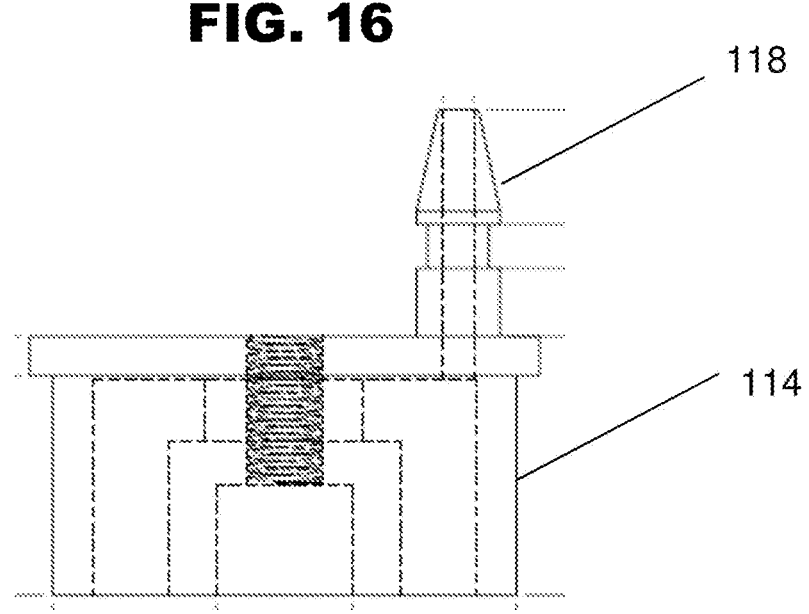
FIG. 16 includes a cross-sectional view illustration of a cap according to an embodiment disclosed herein.
Figure 17:
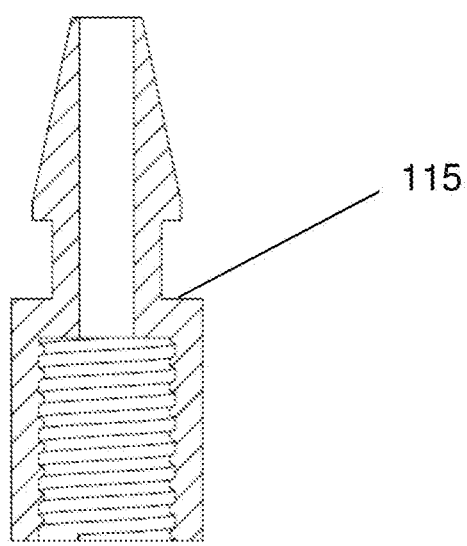
FIG. 17 includes a cross-sectional view illustration of a port according to an embodiment disclosed herein.

The vent port 18 can be engaged with the vent bore 17 and maintain a fluid connection with a filter. In certain embodiments, the vent port 18 can selectively vent the cavity 13 of the vessel 11 at various heights. The vent port 18 can be engaged with, such as in fluid communication with, the filter (not illustrated), such as via the tubing connecter to the filter on one end and connected to the tubing connector of the vent port 18 on the other end. The filter can include a variety of filters depending on the desired application. In other embodiments, as illustrated in FIG. 16, the vent port 118 can be fixed at a certain height within the cavity of the vessel or may not extend into the cavity of the vessel from the cap. In particular embodiments, the vent port 118 can be a contiguous piece of the cap 114.

Referring to FIGS. 11 and 12, a port of the port structure 40 can include a cap portion 41 sized to be disposed within a bore in the cap 14. In certain embodiments, a port of the port structure 40 can include an interior portion 42 extending from the cap portion 41 into the cavity 13 of the vessel 11. In further embodiments, the interior portion 42 of the port can be an extension of the cap portion 41 that extends beyond the cap 14 into the cavity 13 of the vessel 11. In particular embodiments of the assembly comprising the adjustable tube, the dynamic mechanism of the tube port 15 can be disposed on the interior portion 42 of the port, or on the cap portion 41 and interior portion 42 of the port.

In certain embodiments, a port of the port structure 40 can include an exterior portion 43 extending from the cap portion 41 away from the cavity 13 of the vessel 11. The exterior portion 43 of the port can include a tubing connector as described below. In particular embodiments, the tubing connector can include a multimodal structure. The multimodal structure can include a bi-modal structure, a tri-modal structure, and the like. In certain embodiments, each of the different modes of the multimodal structure can have a height in a range of 0.1 to 0.5 inches, such as 0.15 to 0.4 inches, such as 0.2 to 0.3 inches. In certain embodiments, each of the different modes of the multimodal structure can have a height that is different than or the same as one or more of the other modes. In more particular embodiments, the multimodal structure of the exterior portion of the port can contribute to the dynamic mechanism of the port.

In certain embodiments, the multimodal structure of the exterior portion 43 of the port can include a tri-modal structure where each of the modes can include a different shape. While the port is not necessarily limited to this tri-modal structure, in particular embodiments, the first mode 44 can include a polyhedron shape, such as a cube or a cuboid, the second mode 45 can include a cylindrical shape, and the third mode 46 can include a truncated cone shape, such as truncated at the inner diameter of the port.

In certain embodiments, the port can have a height Hp measured from the end of the interior portion to the opposite end of the exterior portion. In particular embodiments, the value for Hp can be at least 1 inch, such as at least 1.25 inches, or eve at least 1.5 inches. In further particular embodiments, the value for $H_P$ may be no greater than 5 inches, no greater than 4 inches, or no greater than 3 inches. For example, the value for $H_P$ can be in a range of any of the above minimum and maximum values, such as 1 to 5 inches, 1.25 to 4 inches, or 1.5 to 3 inches.

As discussed above, the engagement of the tube 10 with the cap 14, such as via the tube bore 16 and tube port 15, is such that the height of the tube 10 relative to the closed end 21 of the vessel 11 is adjustable. In certain embodiments of the assembly comprising the adjustable tube, the height of the tube 10 relative to the closed end 21 of the vessel 11 is adjustable while maintaining an aseptic environment within the cavity 13 of the vessel 11. In particular embodiments, the tube 10 can be adjusted to be in contact with a sidewall 12 of the vessel 11. In more particular embodiments, the tube 10 can be adjusted to a height of at least 0.5 inches from the closed end 21 of the vessel 11, such as a height of at least 1 inch from the closed 21 end of the vessel 11, or even a height of at least 2 inches from the closed end 21 of the vessel 11. In yet further embodiments, the tube can be adjusted up to a distance of at least 1 inch, such as at least 2 inches, such as at least 3 inches from the closed end 21 of the vessel 11.

In other embodiments, the height of the tube can be selected prior to forming the closed system and fixed at the selected height within the closed system. In particular embodiments, the tube can be fixed at a height of at least 5 cm from the closed end of the vessel, such as a height of at least 3 cm from the closed end of the vessel, or even a height of at least 1.5 cm from the closed end of the vessel.

As discussed above, the assembly 5 can provide an increased cell recovery rate as compared to conventional cell recovery assemblies. For example, in certain embodiments, the assembly 5 can have a cell recovery rate of at least 30%, such as at least 50%, or even at least 75% as measured to the Cell Recovery Test. The Cell Recovery Test measures the number of cells recovered as compared to a theoretical number of cells that could be recovered. In particular, a volume of media including a total number of cells is disposed in a vessel described herein. The volume of media is centrifuged using a centrifuge at a speed for a period of time to provide a pellet of cells disposed in the media. The tube is then adjusted to recover a maximum number of cells from the pellet. The maximum number of cells is measured and compared to the total number of cells in the volume of media.

The assembly 5 can be adapted for a variety of applications. In certain embodiments, the assembly 5 can be adapted to handle biologically active material. In certain embodiments, the assembly 5 is adapted to reduce the volume of a composition comprising a media and a biologically active substance, and recover the biologically active substance. In certain embodiments, the assembly 5 is adapted for volume reduction and recovery of cells for cell therapy treatments. In certain embodiments of the assembly comprising the adjustable tube, the assembly 5 is adapted to maintain an aseptic seal with the interior cavity of the vessel when adjusting the height of the dip tube.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. An assembly comprising:
a vessel having an interior cavity;
an adjustable dip tube adapted to selectively withdraw an isolated component at different heights in the vessel,
wherein the assembly is adapted to maintain an aseptic interior cavity when the adjustable dip tube is adjusted to the different heights.

Item 2. An assembly comprising:
a cap adapted to enclose a vessel, wherein the cap comprises a first bore extending through the cap;
a first port adapted to engage with the first bore; and
an adjustable dip tube adapted to engage with the first port and adapted to selectively withdraw an isolated component at different heights in the vessel.

Item 3. An assembly comprising:
a vessel having an open end, a closed end, and an interior cavity;
a cap disposed over the open end of the vessel;
a dip tube having an end coupled to the cap and an opposite end extending a majority of the length of the interior cavity of the vessel, the dip tube adapted to selectively withdraw an isolated component in the vessel,
wherein the assembly is adapted to maintain an aseptic interior cavity when the dip tube withdraws the isolated component in the vessel.

Item 4. The assembly of any one of the preceding items, wherein the assembly comprises a vessel having an interior cavity.

Item 5. The assembly of any one of the preceding items, wherein the assembly comprises a vessel having an open end having a maximum width $W_V$ in a range of 0.3 inches to 3 inches, such as 0.4 inches to 2.5 inches, or even 0.5 inches to 2 inches.

Item 6. The assembly of any one of the preceding items, wherein the assembly comprises a vessel having a height $H_V$ in a range of 3 to 10 inches, 3.5 to 8 inches, or 4 to 6 inches.

Item 7. The assembly of any one of the preceding items, wherein the vessel is a conical tube, a beaker, or a flask.

Item 8. The assembly of any one of the preceding items, wherein the dip tube is adapted to selectively withdraw an isolated component from the vessel at different heights while maintaining an aseptic interior cavity.

Item 9. The assembly of any one of the preceding items, wherein the dip tube includes a multimodal inner diameter.

Item 10. The assembly of item 9, wherein the multimodal inner diameter is a bimodal diameter.

Item 11. The assembly of item 10, wherein the dip tube includes a first end having a first inner diameter and an opposite second end including a second inner diameter, wherein the first inner diameter is greater than the second inner diameter.

Item 12. The assembly of any one of the preceding items, wherein the cap is adapted to maintain an aseptic environment within the vessel.

Item 13. The assembly of any one of the preceding items, wherein the cap comprises a first bore extending through the cap.

Item 14. The assembly of any one of the preceding items, wherein the cap comprises a first bore extending through the cap and a second bore extending through the cap.

Item 15. The assembly of item 14, wherein the first bore is a center bore and the second bore is an off-center bore.

Item 16. The assembly of any one of the preceding items, wherein the first bore is adapted to receive the dip tube.

Item 17. The assembly of any one of the preceding items, wherein the second bore is adapted to receive a vent tube.

Item 18. The assembly of item 17, wherein the vent tube is in fluid connection with a filter.

Item 19. The assembly of any one of the preceding items, wherein the assembly comprises a first port.

Item 20. The assembly of any one of the preceding items, wherein the first port is disposed within the first bore and extending through the cap.

Item 21. The assembly of any one of the preceding items, wherein the assembly comprises a first port, wherein at least a portion of the first port comprises threading, and wherein the first bore comprises threading, and wherein the threading on the first bore is adapted to engage with the threading on the first port.

Item 22. The assembly of any one of the preceding items, wherein the first port comprises a tubing connector.

Item 23. The assembly of item 22, wherein the tubing connector on the first port is disposed outside of the interior cavity of the vessel.

Item 24. The assembly of any one of the preceding items, wherein the dip tube is adapted to engage with the first port.

Item 25. The assembly of any one of the preceding items, wherein the dip tube comprises threading, and wherein the first bore comprises threading, and wherein the threading on the dip tube is adapted to engage with the threading on the first bore.

Item 26. The assembly of any one of the preceding items, wherein the assembly comprises a second port.

Item 27. The assembly of any one of the preceding items, wherein the second port is disposed within the second bore and extending through the cap.

Item 28. The assembly of any one of the preceding items, wherein at least a portion of the second port comprises threading, and wherein the second bore comprises threading, and wherein the threading on the second bore is adapted to engage with the threading on the second port.

Item 29. The assembly of any one of the preceding items, wherein the second port comprises a tubing connector.

Item 30. The assembly of any one of the preceding items, wherein the tubing connector on the second port is disposed outside of the interior cavity of the vessel.

Item 31. The assembly of any one of the preceding items, wherein the second port is adapted to vent the interior cavity of the vessel.

Item 32. The assembly of any one of the preceding items, wherein the second port is adapted to be in fluid communication with a filter.

Item 33. The assembly of any one of the preceding items s, wherein the second port is adapted to selectively vent the interior cavity of the vessel at various heights.

Item 34. The assembly of any one of the preceding items, wherein the assembly comprises a dynamic mechanism configured to allow the height of the tube to be adjusted while withdrawing the isolated component and maintaining an aseptic interior cavity.

Item 35. The assembly of any one of the preceding items, wherein the dip tube is adapted to be adjustable by a height of at least 0.5 inches, at least 1 inch, or at least 2 inches.

Item 36. The assembly of any one of the preceding items, wherein the assembly comprises a static mechanism configured to fix the height of the tube at a specific height while withdrawing the isolated component and maintaining an aseptic interior cavity.

Item 37. The assembly of any one of the preceding items, wherein the dip tube is fixed within the assembly at a height of at least 0.5 inches, at least 1 inch, or at least 2 inches.

Item 38. The assembly of any one of the preceding items, wherein the dip tube is adapted to handle biologically active material.

Item 39. The assembly of any one of the preceding items, wherein the assembly is adapted to handle biologically active material.

Item 40. The assembly of any one of the preceding items, wherein the assembly is adapted to reduce the volume of a composition comprising a media and a biologically active substance, and recover the biologically active substance.

Item 41. The assembly of any one of the preceding items, wherein the assembly is adapted for volume reduction and recovery of cells for cell therapy treatments.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. An assembly comprising:
a vessel having an interior cavity, the vessel having a closed end and a tube port opposite the closed end, the tube port having a first bore;
an adjustable dip tube configured to be placed within the interior cavity and adapted to withdraw an isolated component in the vessel at different heights with respect to the closed end,
wherein the assembly is adapted to maintain an aseptic, interior cavity as the adjustable dip tube is adjusted to the different heights relative to the closed end,
wherein the assembly comprises a dynamic mechanism comprising the adjustable dip tube and the first bore,
wherein the adjustable dip tube comprises threading, and wherein the first bore comprises threading, and wherein the threading on the adjustable dip tube is adapted to engage with the threading on the first bore, wherein the first bore permits a fluid connection between the interior cavity and an exterior environment outside the adjustable dip tube,
wherein the threading of the first bore extends into the interior cavity, and
wherein the dynamic mechanism is configured to allow the height of the adjustable dip tube to be adjusted with respect to the closed end while withdrawing the isolated component and maintaining the aseptic interior cavity.

2. The assembly of claim 1, wherein the dip tube includes a first end having a first inner diameter and second end axially opposite the first end including a second inner diameter, wherein the first inner diameter is greater than the second inner diameter.

3. The assembly of claim 1, wherein the dip tube includes a first end having a first outer diameter and a second end axially opposite the first end including a second outer diameter, wherein the first outer diameter is greater than the second outer diameter.

4. The assembly of claim 1, wherein the assembly comprises a vent port adapted to selectively vent the interior cavity of the vessel at various heights.

5. The assembly of claim 1, wherein the dip tube is adapted to be adjustable by a height of at least 0.5 inches.

6. The assembly of claim 1, wherein the dip tube is fixed within the assembly at a height of at least 0.5 inches.

7. The assembly of claim 1, wherein the dip tube is adapted to handle biologically active material.

8. The assembly of claim 1, wherein the assembly is adapted to handle biologically active material.

9. The assembly of claim 1, wherein the assembly is adapted to reduce the volume of a composition comprising a media and a biologically active substance, and recover the biologically active substance.

10. The assembly of claim 1, wherein the assembly is adapted for volume reduction and recovery of cells for cell therapy treatments.

\* \* \* \* \*